(12) United States Patent
Bentine et al.

(10) Patent No.: US 12,714,317 B2
(45) Date of Patent: Aug. 25, 2026

(54) VASCULAR IMAGING DEVICE

(71) Applicant: Oxford University Innovation Limited, Oxford (GB)

(72) Inventors: Elliot Bentine, Oxford (GB); Winok Lapidaire, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 324 days.

(21) Appl. No.: 18/280,278

(22) PCT Filed: Mar. 9, 2022

(86) PCT No.: PCT/GB2022/050615
§ 371 (c)(1),
(2) Date: Sep. 5, 2023

(87) PCT Pub. No.: WO2022/189789
PCT Pub. Date: Sep. 15, 2022

(65) Prior Publication Data

US 2024/0065557 A1 Feb. 29, 2024

(30) Foreign Application Priority Data

Mar. 9, 2021 (GB) ...................................... 2103265

(51) Int. Cl.
*A61B 5/02* (2006.01)
*A61B 5/00* (2006.01)
*G06T 7/00* (2017.01)

(52) U.S. Cl.
CPC ........ *A61B 5/02007* (2013.01); *A61B 5/0002* (2013.01); *A61B 5/004* (2013.01);
(Continued)

(58) Field of Classification Search
CPC ... A61B 5/02007; A61B 5/0002; A61B 5/004; A61B 5/0062; A61B 5/6816;
(Continued)

(56) References Cited

U.S. PATENT DOCUMENTS 5,251,025 A 10/1993 Cooper et al.
5,741,213 A * 4/1998 Kouchi .................. G06V 20/69 600/407
(Continued)

FOREIGN PATENT DOCUMENTS

WO 2018/235091 A2 12/2018
WO 2019/204211 A1 10/2019

OTHER PUBLICATIONS

Billaud et al.—A new method for in vivo visualization of vessel remodeling using a near-infrared dye (2011).
(Continued)

*Primary Examiner* — Abid A Mustansir
(74) *Attorney, Agent, or Firm* — Thomas|Horstemeyer, LLP

(57) ABSTRACT

A vascular imaging device has a casing having a first casing portion (4) and a second casing portion (5). The first casing portion and the second casing portion together define a gap (10) therebetween for receiving an auricle of a subject. The device also includes light source (12) and an image sensor (20) both mounted on the casing. The light source is arranged to transmit light to illuminate an auricle placed within the gap. The image sensor is arranged to detect light transmitted by the light source and output image data representative of the light received at the image sensor.

15 Claims, 12 Drawing Sheets

(52) U.S. Cl.
CPC .......... *A61B 5/0062* (2013.01); *A61B 5/6816* (2013.01); *A61B 5/6838* (2013.01); *G06T 7/0012* (2013.01); *A61B 2560/02* (2013.01); *A61B 2560/0406* (2013.01); *A61B 2560/0462* (2013.01); *A61B 2562/0238* (2013.01)

(58) Field of Classification Search
CPC .............. A61B 5/6838; A61B 2560/02; A61B 2560/0406; A61B 2560/0462; A61B 2562/0238; A61B 5/0059; A61B 5/489; G06T 7/0012
See application file for complete search history.

(56) References Cited

U.S. PATENT DOCUMENTS

| | | | | |
|---|---|---|---|---|
| 2007/0293766 | A1* | 12/2007 | Bakker | G01N 21/59 356/326 |
| 2009/0245601 | A1* | 10/2009 | Cohen | A61B 5/0059 382/128 |
| 2012/0108898 | A1 | 5/2012 | Viola | |
| 2013/0204112 | A1 | 8/2013 | White et al. | |
| 2013/0303864 | A1* | 11/2013 | Chen | A61B 5/6838 600/340 |
| 2017/0303830 | A1* | 10/2017 | Klein | A61B 5/0075 |

OTHER PUBLICATIONS

Honkura et al.—Intravital imaging-based tools for vessel identification and assessment of concurrent dynamic vascular events (2018).
Yamazaki et al.—Whole-mount Confocal Microscopy for Adult Ear Skin (2018).
International Search Report and Written Opinion for WO 2022/189789 (PCT/GB2022/050615), dated May 25, 2022, pp. 1-9.
UK Search Report for GB 2103265.1, dated Oct. 5, 2021, pp. 1-4.
European Communication for Patent Application No. 22 709 792.0, dated May 23, 2025, pp. 1-8.

* cited by examiner

VASCULAR IMAGING DEVICE

CROSS-REFERENCE TO RELATED APPLICATIONS

This application is the National Stage of International Application No. PCT/GB2022/050615, filed Mar. 9, 2022, which claims priority to GB 2103265.1, filed Mar. 9, 2021, which are entirely incorporated herein by reference.

The present invention relates to a vascular imaging device, particularly a vascular imaging device for the auricle.

The imaging of blood vessels is an important tool in the diagnosis and monitoring of Alzheimer's disease and cardiovascular diseases (CVDs). CVDs are a group of disorders of the heart and blood vessels, and are the leading causes of death globally. According to the World Health Organisation, more than 17 million died from CVDs in 2016, accounting for 31% of all deaths. It has been shown that CVDs cause structural changes to vasculature, such as to vessel tortuosity, arborisation, and the ratio of veins to arteries, which are detectable through imaging methods.

Retinal imaging is an affordable technique that provides detailed images of blood vessels. Owing to the close anatomical proximity between the eye and the brain vasculature, retinal vascular imaging has been used to diagnose cerebrovascular disease.

However, owing to the sensitivity of the retina, the light intensity required to obtain an image having sufficient contrast to be able to carry out analysis may be too bright for the subject to endure safely. Therefore, lower intensities of light are conventionally used in combination with a longer exposure time. Consequently, retinal imaging relies on the subject maintaining a steady gaze without blinking. This can be difficult for many subjects, such as children or those with certain clinical conditions (e.g. vascular dementia), to achieve. This means that images obtained using retinal imaging can be blurry or dark. To compensate for this, it is often necessary to capture and subsequently analyse multiple images in order to obtain a usable result, which can be a time-consuming process. Furthermore, owing to the typically large size of retinal imaging machines, it is often impractical for these machines to be moved (e.g. between patients). This can restrict the care that can be given to patients, particularly those who are bedridden.

An alternative imaging technique involves magnetic resonance imaging (MRI) using time-of-flight or contrast angiography. However, MRI machines are large, stationary and expensive both to acquire and to operate. Images produced by MRI machines can also be insufficiently detailed for small vasculature to be analysed. Furthermore, contrast angiography is an invasive technique, requiring the injection of a contrast agent into the body of the subject. This can not only be uncomfortable, but can cause an adverse reaction in some subjects. MRI machines are also not safe for subjects with metal implants or pacemakers.

Therefore, the Applicant has identified that there is a need for an improved vascular imaging device that overcomes the above-mentioned shortcomings.

When viewed from a first aspect, the invention provides a vascular imaging device comprising:

a casing, comprising a first casing portion and a second casing portion, wherein the first casing portion and the second casing portion together define a gap therebetween for receiving an auricle of a subject;

a light source, mounted on the casing; and an image sensor, mounted on the casing;

wherein the light source is arranged to transmit light to illuminate an auricle placed within the gap; and wherein the image sensor is arranged to:

detect light transmitted by the light source; and output image data representative of the light received at the image sensor.

When viewed from a second aspect, the invention provides a method of operating a vascular imaging device, the device comprising:

a casing, comprising a first casing portion and a second casing portion, wherein the first casing portion and the second casing portion together define a gap therebetween for receiving an auricle of a subject;

a light source, mounted on the casing; and an image sensor, mounted on the casing;

wherein the light source is arranged to transmit light to illuminate an auricle placed within the gap and the image sensor is arranged to detect light transmitted by the light source and to output image data representative of the light received at the image sensor;

the method comprising:

positioning an auricle of a subject within the gap;

receiving, at the image sensor, light transmitted from the light source through, or reflected from, the auricle;

generating, from image data provided by the image sensor, an image of blood vessels within the auricle.

Thus it will be seen that the present invention provides a vascular imaging device and method that may be used to generate an image of blood vessels within the auricle (the projecting portion of the ear) of a subject. The auricle can be positioned within the gap defined by the casing and then be illuminated by a light source. This allows an image sensor (and any other optical components of the device) to generate an image of the blood vessels within the auricle.

The light source and the image sensor may be arranged on opposite sides of the gap, meaning that light from the light source may be directed through the auricle from one side of the auricle to the other (such that the line traversing the gap, e.g. between the light source and the image sensor, may define an optical axis of the device). This allows transmission imaging methods to be used. The light source and the image sensor may be arranged on the same side of the gap, in which case reflection or backscattering imaging methods may be used. These methods will be described in more detail below.

The Applicant has identified that imaging blood vessels within the ear is beneficial for a number of reasons. Firstly, both sides of the ear are accessible, meaning that light transmission imaging methods may be used. This contrasts with retinal imaging, in which clinicians rely on light reflection methods, as only one side of the eye is accessible. Light transmission imaging methods, such as dark-field imaging, phase contrast imaging and polarisation-sensitive detection are capable of identifying features that are invisible to reflection imaging techniques. For example, polarisation imaging can be used to detect birefringence in collagen, the main matrix protein of the artery wall.

Applying vascular imaging techniques to the auricle also allows a higher light intensity to be used as, unlike the retina, the auricle is not sensitive to high intensity light. This means that a shorter exposure time is required in order to generate each usable image. Moreover, using a higher light intensity reduces the risk of obtaining dark or blurred images, e.g. as a result of the movement of the subject. Thus, the efficiency of the imaging process from both a time and cost perspective may be improved, as well as the quality of the generated image.

Furthermore, devices in accordance with the present invention may be produced using inexpensive components, which contrasts with time-of-flight angiography methods requiring expensive MRI machines. Owing to the image resolutions attainable using MRI time-of-flight angiography methods, it can also prove difficult (or even impossible) to generate images of small blood vessels. The magnetic field strength that can be used with MRI methods is limited, as high magnetic field strengths can be dangerous for subjects and may introduce noise and artefacts into the generated images. However, devices in accordance with the present invention can avoid such limitations, so can produce images of higher resolution than those produced using MRI time-of-flight angiography methods.

The casing may be manufactured from any suitable or desired material. Preferably the material is rigid, so as to protect the components contained therein from being damaged (e.g. by impact or by dust or dirt). Preferably the device is portable, e.g. hand-held. This can improve the ease with which the device is operated. A lightweight material (e.g. a polymer) may be selected to improve portability of the device.

The first casing portion and the second casing portion may be any suitable size and shape, e.g. so that they fit comfortably around the auricle of a (e.g. human) subject.

In one embodiment the second casing portion is longitudinally extended, e.g. having a length (e.g. in a direction parallel to the optical axis) that is greater than a width (and, e.g., a depth) of the second casing portion. Preferably the optical axis extends through the second casing portion in a direction perpendicular to the opposing surface(s) of the first and/or second casing portions, e.g. along a central axis of the second casing portion.

Preferably the second casing portion (e.g. has a width (e.g. a dimension in a direction perpendicular to the optical axis) that) tapers towards an end of the second casing portion that is proximal to the gap, e.g. the second casing portion tapers towards the first casing portion. The second casing portion may thus have a conical end (proximal to the gap). This helps the device to be located around the auricle of a subject and helps to present a smaller clamping area than the cross-sectional area of the main body of the second casing portion, thus allowing the device to be used with smaller auricles.

Preferably the first casing portion (e.g. has a width (e.g. a dimension in a direction perpendicular to the optical axis) that) tapers towards an end of the first casing portion that is proximal to the gap, e.g. the first casing portion tapers towards the second casing portion. Preferably the first casing portion (e.g. has a width (e.g. a dimension in a direction perpendicular to the optical axis) that) tapers towards the optical axis (e.g. in a direction perpendicularly to the direction in which the second casing portion is longitudinally extended). Preferably the first casing portion (e.g. has a width (e.g. a dimension in a direction perpendicular to the optical axis) that) tapers away from a connection (e.g. a rod or a hinge) between the first casing portion and the second casing portion.

Again, this helps the device to be located around the auricle of a subject and helps to present a smaller clamping area than the cross-sectional area of the main body of the second casing portion, thus allowing the device to be used with smaller auricles.

The gap defined between the first casing portion and the second casing portion may be any suitable size and shape for receiving the auricle of a (e.g. human) subject. The gap may be shaped and sized to receive any part of the auricle.

Preferably the gap is defined between opposing surfaces of the first casing portion and the second casing portion. The distance between the opposing surfaces (i.e. the width of the gap) may be between 2 mm and 20 mm, e.g. between 5 mm and 10 mm, e.g. approximately 8 mm (e.g. in a clamped position, as described below).

Preferably, the width of the gap (e.g. in the clamped position) is equal to or smaller than the width of the auricle of the subject.

Thus, when the auricle is arranged within the gap, preferably the device is arranged such that (e.g. in the clamped position) both opposing surfaces are in contact with (opposite sides of) the auricle. Thus, the auricle can be held still (relative to the light source and the image sensor) while image data is being generated, which allows a higher quality image to be obtained. As the auricle is held by the device itself, the ease with which the imaging process can be performed can also be increased.

These benefits contrast with retinal imaging methods, during which it can be difficult to ensure that the eye of the subject does not move relative to the image sensor, which can cause blurring of the image. This also helps to limit the intensity of ambient light that is received by the image sensor, thereby helping to increase further the quality of the captured image.

The opposing surfaces of the first casing portion and the second casing portion may be substantially parallel (e.g. in at least the clamped position) so as to define a gap of uniform width. This helps to avoid protrusions that may pinch the auricle of the subject and cause discomfort. However, in some embodiments, the opposing surfaces may comprise contours, e.g. shaped to accommodate an auricle of non-uniform width. The opposing surfaces may be moulded to match the shape of a particular auricle (e.g. of a particular subject). This can improve the comfort of the subject and help to limit the intrusion of ambient light into the portion of the auricle that is to be imaged, thereby improving image quality.

In some embodiments one or, preferably, both opposing surfaces comprise a soft padding material. This material may comprise a deformable material, e.g. rubber or foam. The deformability of the soft padding can improve the comfort of the subject, but can also help to ensure that ambient light is occluded from the area of the auricle that is exposed to light from the light source, by deforming around the contours of the subject's auricle. This can improve the quality of the image that can be produced, allowing more accurate clinical analysis to be undertaken.

In some embodiments one or, preferably, both opposing surfaces comprise a removable (e.g. disposable) element, which may comprise a soft or deformable padding material, such as silicon. This may help prevent cross-contamination between subjects, increase the comfort for the subjects and improve the quality of the images by improving the ability of the device to retain the auricle.

In some embodiments one or, preferably, both opposing surfaces comprise a portion having a hard surface (and, e.g. a portion having a soft surface). This may help the opposing surface(s) to press onto the auricle, to cause the ear to conform to the respective surface(s). This help to constraint the surface and/or shape that is being imaged to the (e.g. curved) ideal object plane of the imaging system, which may help to increase the imaging resolution.

In some embodiments, the light source is mounted on the first casing portion and the image sensor is mounted on the second casing portion. In some embodiments, the light source is mounted on the second casing portion and the image sensor is mounted on the first casing portion. Thus, in such embodiments, the light source and the image sensor are separated by the gap defined by the first and the second casing portions. This allows transmission imaging methods to be used, in which the light source is arranged to transmit light directly towards the image sensor through the auricle (arranged within the gap), from one side of the auricle to the other. In some embodiments, the light source and the image sensor are mounted on the same casing portion (e.g. on the first casing portion or on the second casing portion). In such embodiments, the light transmitted by the light source is reflected or backscattered from the auricle (arranged within the gap) and is received by the image sensor. Thus, this arrangement allows reflection or backscattering imaging methods to be used.

In some embodiments the light source is mounted on the optical axis and, e.g., arranged to direct light along the optical axis towards the image sensor.

In some embodiments the light source is mounted off (spaced from) the (main) optical axis (along which light is directed across the gap, e.g. perpendicular to the opposing surfaces of the first and second casing portions). Thus preferably the optical axis and/or the central axis of the second casing portion does not pass through the light source. Preferably the device comprises one or more lenses, one or more optical fibres and/or one or more mirrors, e.g. mounted in the first casing portion and, arranged to direct the light from the light source (e.g. onto and along the optical axis) to the image sensor (e.g. across the gap). Using an optical fibre may allow the light source to be mounted in the second casing portion.

Positioning the light source and folding the optical path away from the optical axis may allow the size of the first casing portion to be reduced (e.g. compared to the light source being on the optical axis), which may help to fit the device behind the auricle of a subject. This configuration also helps to move the light source (and the heat it emits) away from the auricle and head of a subject, which helps to improve the subject's comfort.

The one or more lenses and/or one or more mirrors may be arranged to spread the light from the light source, e.g. over an area that is larger than the area over which light is emitted from the light source. This helps to widen the light to fill the aperture(s) (e.g. in the first and second casing portions).

In some embodiments, the device comprises a first image sensor, mounted on the first casing portion with the light source, and a second image sensor mounted on the second casing portion. In this case, the first image sensor may be arranged to detect reflected or backscattered light from the auricle and the second image sensor may be arranged to detect light transmitted directly through the auricle. In another set of embodiments, the device comprises a first light source, mounted on the first casing portion with the image sensor, and a second light source mounted on the second casing portion. The image sensor may be arranged to detect reflected or backscattered light from the first light source and to detect light transmitted directly through the auricle from the second light source. The first light source and the second light source may be configured to illuminate the auricle consecutively (e.g. alternately). Embodiments comprising a single sensor and multiple light sources may advantageously be less expensive than embodiments comprising multiple sensors.

In the above-described sets of embodiments, both reflection and transmission imaging techniques can be performed by the same device. Thus, it will be appreciated that, in comparison with retinal imaging for which transmission methods are not practicable, the present invention can increase the range of imaging methods that can be used to generate an image of a subject's blood vessels.

In some embodiments the device comprises a first clamping member mounted on the first casing portion. The device may further comprise a second clamping member mounted on the second casing portion. Preferably the first clamping member and the second clamping member together define a clamp for holding the auricle of the subject therebetween. Preferably the first clamping member is movable (e.g. with the first casing portion) between an unclamped position and a clamped position. The first clamping member and the second clamping member may comprise the opposing surfaces of the first and second casing portions (i.e. together defining the gap). Preferably the (e.g. opposing surfaces of the) first and second casing portions are arranged to mate with each other, e.g. the opposing surfaces conform to each other.

The first clamping member may be arranged on the first casing between the light source and the gap. In some embodiments, the first clamping member comprises an aperture for allowing light emitted by the light source to travel into the gap.

In some embodiments the first casing portion is movable relative to the second casing portion. It will be appreciated that relative movement between the first casing portion and the second casing portion allows the (e.g. minimum) width of the gap to be varied. This can improve the ease with which the auricle of a subject can be positioned within the gap, and also allows the device to be used for a variety of subjects having different auricle shapes and sizes.

The first casing portion may be (e.g. detachably) mounted on the second casing portion. The first casing portion may be hingedly movable relative to the second casing portion.

Preferably the first casing portion is slidably (e.g. linearly) movable relative to the second casing portion. Preferably the first casing portion is able to be moved linearly, in a direction parallel to the optical axis, relative to the second casing portion. This may help to keep the opposing surfaces of the first and second casing portions parallel to each other as the first and second casing portions are moved relative to each other. This helps to apply an even pressure to the auricle, so to keep the auricle flat with respect to the imaging system and to illuminate the auricle evenly.

In one embodiment the device comprises a rod that extends (e.g. across the gap, e.g. spaced from (and, e.g., parallel to) the optical axis) between the first casing portion and the second casing portion. The rod preferably connects the first casing portion and the second casing portion. Preferably the rod is slidably mounted to the first casing portion and/or the second casing portion, so to slidably move the first casing portion relative to the second casing portion. Preferably the first casing portion is fixedly mounted to the rod (e.g. there is no relative movement between the rod and the first casing portion). Preferably the rod is slidably mounted in the second casing portion.

The first casing portion may be movable relative to the second casing portion between an unclamped position, in which the first casing portion is moved away from the second casing portion, and a clamped position, in which the first casing portion is moved towards the second casing portion. Thus, in the unclamped position, the (e.g. minimum) width of the gap is greater than in the clamped position. The (e.g. minimum) width of the gap in the unclamped position may be between 10 mm and 40 mm, e.g. between 15 mm and 30 mm, e.g. approximately 25 mm.

In use, the first casing portion may be moved to the unclamped position to facilitate the location of the subject's auricle within the gap prior to obtaining an image, then moved to the clamped position in order to secure the auricle in place (e.g. between the first clamping member and the second clamping member). When it is desired to remove the auricle from the gap (e.g. after an image has been obtained), the first casing portion may be moved to the unclamped position so as to facilitate release and removal of the subject's auricle from the gap.

In some embodiments, the device comprises a biasing member arranged to bias the first casing portion (towards the second casing portion) into the clamped position. The device may comprise a stop for the first casing portion to prevent the first casing portion contacting the second casing portion, so that a minimum width of the gap (in the clamping position) is maintained. The biasing member may comprise a spring, e.g. a torsion, extension or compression spring. The biasing member may comprise a magnet.

The provision of a biasing member can help to ensure that the auricle is held within the gap with sufficient force to obtain a high quality image. Said force is preferably sufficient to ensure that the auricle of the subject is held securely within the gap (e.g. by the first and second clamping members). The force of the biasing member may also serve to flatten or stretch the auricle so that the area of the auricle that the light source is arranged to illuminate can be held substantially within the same plane (e.g. the focal plane of the optical components of the device). This helps to increase the resolution of the generated image.

When the first casing portion is hingedly movable relative to the second casing portion, the biasing member may be mounted (e.g. in a hinge) between the first casing portion and the second casing portion.

When the first casing portion is slidably (e.g. linearly) movable relative to the second casing portion, the biasing member may be mounted in the second casing portion, e.g. away from the gap. The biasing member may be arranged to act on the rod (e.g. that connects the first casing portion to the second casing portion), so to bias the first casing portion towards the second casing portion.

In some embodiments the (e.g. the second casing portion of the) device comprises an actuator arranged to move the first casing portion relative to the second casing portion, e.g. against the bias of the biasing member. The type of actuator may depend on the way in which the first casing portion is arranged to move relative to the second casing portion. For example, the actuator may comprise a rotatable actuator when the first casing portion is hingedly movable relative to the second casing portion.

The actuator may comprise a slidable actuator when the first casing portion is slidably movable relative to the second casing portion. The slidable actuator may be connected to the rod and arranged to actuate the rod to move the first casing portion relative to the second casing portion. Providing the actuator on the second casing portion may help a user to operate the device single handedly.

In some embodiments, the device comprises one or more sensors for determining the position of the first casing portion (e.g. relative to the second casing portion). This determination may provide an indication of whether the first casing portion is in the clamped position or the unclamped position. The one or more sensors may be configured to determine whether an auricle of a subject is (e.g. sufficiently) held between the first casing portion and the second casing portion. The one or more sensors may comprise pressure sensors.

In some embodiments the first casing portion and/or the second casing portion defines a bore extending into the first and/or second casing portion from an aperture defined on the (e.g. opposing) surface of the first and/or second casing portion (e.g. the surface of the first and/or second clamping member) that defines the gap. The image sensor may be arranged within the bore. This helps to protect the image sensor from damage and to reduce the intensity of ambient light that is detected by the image sensor, which can increase the quality of the captured image.

Thus, the light transmitted across the gap by the light source or reflected from the auricle is preferably directed through the bore to the image sensor. This arrangement can increase the likelihood that, when the auricle is positioned within the gap and is illuminated by the light source, the image sensor is arranged to detect (only) the light propagating through the auricle.

The aperture(s) defined on the (e.g. opposing) surface(s) of the first and/or second casing portion(s) and/or the bore extending into the first and/or second casing portion from the aperture(s) may have any suitable and desired maximum dimension (e.g. diameter, e.g. in a direction perpendicular to the optical axis). In one embodiment the aperture(s) and/or the bores have a maximum dimension greater than 2 mm, e.g. greater than 4 mm, e.g. approximately 5 mm. This helps to increase the field of view, e.g. to allow images to be captured over a relatively large area of the auricle.

The light source may comprise any suitable light-emitting device. The light source may comprise a laser. Preferably, the light source comprises a light-emitting diode (LED). The light source may be configured to emit a single wavelength of light. However, in preferred embodiments, the light source is configured to emit multiple wavelengths of light.

The light source may be configured to emit light having a wavelength between 500 nm and 570 nm, e.g. between 510 nm and 540 nm, e.g. approximately 523 nm (green light). The light source may be configured to emit light having a wavelength between 600 nm and 750 nm, e.g. between 630 nm and 650 nm, e.g. approximately 640 nm (red light). The light source may be configured to emit light having a wavelength between 400 nm and 450 nm (blue light). The light source may be configured to emit multiple wavelengths of light in any suitable or desired combination. The light source may be configured to emit multiple wavelengths simultaneously or consecutively. Preferably, the light source is configured to emit (e.g. simultaneously) both red light and green light.

The wavelength of the green light may be selected to be close to the wavelength of maximum absorbance for both oxygenated and deoxygenated blood. This increases the contrast between blood vessels and surrounding media (e.g. skin tissue), thereby allowing blood vessels to be identified. The wavelength of the red light may be selected to allow a distinction to be made between arteries and veins, owing to differences in oxygenated haemoglobin content. The short wavelengths of the light increase the attenuation of the light travelling through the blood vessels, thereby improving image contrast. Thus the wavelengths of the light are particularly suitable for imaging blood vessels.

The device may comprise one or more lenses (e.g. an optical system) for focusing (an image of) the portion of the auricle to be imaged onto the image sensor. One or more of the lenses may be mounted on the first casing. In some embodiments one or more of the lenses are mounted on the second casing portion. One or more of the lenses may be mounted within the bore of the first and/or second casing portion. One or more of the lenses may be movable relative to the light source, the gap and/or the image sensor (e.g. along the light path between the light source and the image sensor). This allows the focus to be adjusted. The device may comprise a fixed lens and a movable focusing lens. One or more of the lenses may comprise a flexible lens, which may be deformed to give a variable (e.g. controllable) focal length.

The device may comprise a lens actuator (e.g. a thumb-wheel) for moving and/or deforming one or more of the lenses. The lens actuator may be manually operated (e.g. by an operator of the device). In some embodiments, the lens actuator is automatically operated (e.g. electrically). The device may comprise an electrical motor arranged to move and/or deform the one or more movable lenses. The electrical motor may comprise a servomotor. The electrical motor may comprise a stepper motor. The electrical motor may comprise a linear actuator (e.g. a solenoid). In some embodiments the image sensor may be moved in order to achieve a similar effect as moving and/or deforming one or more of the lenses.

Providing a lens actuator that is automatically operated (e.g. to provide an autofocus adjustment) may help to allow relatively high resolution images to be made of the auricle, which has a thickness that does not lie entirely within the focal plane. This may be achieved by scanning the focal plane and capturing images in different focal planes (e.g. image slices through the depth of the auricle). Thus, preferably, the depth of field of the device is (e.g. significantly) less than the width of the gap (and thus the thickness of an auricle to be imaged). The images may then be post processed, e.g. to produce a single image which is in focus everywhere (e.g. through the depth of the auricle).

This helps to allow the auricle to be imaged accurately. The captured images may be analysed, e.g. to identify where blurred and/or in focus parts of each image are present. Thus may allow a 3D image to be generated, which helps to enable vessels in the non-flat material of the auricle to be imaged, as the vessels may cross each other. Furthermore, use of a scanned or auto focus may help to provide a device that is able to be operated by a non-skilled operator, while still allowing high quality images to be captured.

The device may comprise any suitable or desired further optical components. The device may comprise a filter. The device may comprise a polarisation filter. This can allow the birefringence in collagen to be detected in the vessel walls of the subject, thereby allowing further insight into the structure of the subject's blood vessels. The filter may be mounted on the device, e.g. within the bore of the device, between the image sensor and the gap. The filter may be removably mounted on the device. Thus, the device may comprise a mount for receiving one or more removable filters. This increases the adaptability and ease of use of the device, as it can allow the operator to easily select and apply appropriate filters, depending on the type of image data that it is desirable to collect.

The image sensor may be a monochromatic image sensor. The image sensor may be a chromatic image sensor (e.g. comprising a Bayer filter). The image sensor may comprise a charge-coupled device (CCD). The image sensor may comprise a complementary metal-oxide-semiconductor (CMOS) sensor. The image sensor may comprise a micro-channel plate (MCP).

In one embodiment (e.g. the second casing portion of) the device comprises an image capture button (e.g. arranged to actuate a switch) arranged to operate (e.g. a shutter of) the image sensor to capture images of the auricle. This may allow the device to be operated single handedly.

The vascular imaging device may comprise a readable memory chip configured to store image data. The device may comprise a transmitter with which the readable memory chip is coupled. The vascular imaging device may comprise a removable storage device, e.g. a Secure Digital (SD) card. Thus, the operator of the device can (e.g. periodically) output image data from the device to a separate device or server for storage or further processing.

The image of blood vessels within the auricle may be an image of the structure of the blood vessels themselves and/or an image of their contents (e.g. blood). By imaging the blood within the blood vessels, measurements of parameters including blood oxygenation may be determined.

The device may further comprise a processor configured to process image data received from the image sensor. The processor may be integrated with the device as a single device—e.g. arranged within or mounted on the casing. Alternatively, the processor may be separate (e.g. remote) from the device. The processor may be communicatively connected to the device (e.g. by cable or other wired or wireless communication link).

In some embodiments, the processor is configured to process image data so as to generate an image for display. The processor may be configured to analyse the image data to determine a value representative of a property of a blood vessel of the subject. The processor may be configured to determine, from the image data, a value representative of blood vessel density. The processor may be configured to determine an estimate of average blood vessel thickness. In some embodiments, the processor is configured to determine a value representative of mean vessel thickness. The processor may be configured to determine an estimate of blood oxygenation and/or vascular reactivity. The processor may be configured to execute image segmentation methods.

The processor may be configured to control the operation of one or more electrical components of the device. In some embodiments, the processor is configured to control the operation of the light source and/or the image sensor. The processor may be configured to control the operation of the lens actuator. The device may comprise one or more user inputs for controlling the operation of the one or more electrical components of the device (e.g. to initiate the generation of an image).

The device may comprise a display for displaying image data. The display may comprise an electronic display screen. The display screen may comprise a liquid crystal display (LCD) screen. The display may comprise one or more LEDs. The display may comprise an electronic ink display screen. The processor may be configured to provide image data to the display. In some embodiments, the processor is configured to provide a determined value representative of a property of a blood vessel to the display.

Although the display may be integrated with the vascular imaging device (e.g. arranged on the casing of the device), in some embodiments the display is comprised within a separate (e.g. remote) auxiliary device (e.g. a smartphone). The vascular imaging device may be communicatively connected to the auxiliary device (e.g. by cable or other wired or wireless communication link).

In some embodiments the device comprises a (e.g. wireless) transmitter. The transmitter may be configured to communicate with an external server or electronic device, such as a mobile phone, PC, etc. The transmitter may be configured to transmit image data (e.g. from the readable memory of the device) to the separate server or electronic device, where it may be stored and/or processed and/or displayed.

The (e.g. processor of the) device may be configured to send image data to the external (e.g. auxiliary) device or server via the transmitter. In some embodiments the device comprises a receiver. The (e.g. processor of the) device may be configured to receive, from an external (e.g. auxiliary) device or server via the receiver, a command signal for controlling the operation of one or more electrical components of the device (e.g. the light source, image sensor, lens actuator etc.). The command signal may be processed by the processor to control the operation of one or more electrical components of the device.

The device may comprise a data logger for storing image data. The image data may be logged by the processor. This can allow image data over time for a particular subject to be reviewed, thereby providing a useful resource for clinicians who may be monitoring the progression of a disease.

The device may be arranged to receive electrical power from an external power source. Preferably the device comprises an integral power supply (e.g. a battery or cell). The integral power supply is preferably rechargeable. This allows the device to be used wirelessly, which increases the ease with which the device can be operated. This allows the device to be portable, e.g. hand-held, which means that image data can be collected more easily. The power supply may be configured to provide electrical power to the light source, the image sensor, the lens actuator and/or the processor (and/or other electrical components of the device).

By monitoring changes in the blood vessels in the subject's ear, clinicians can infer details of changes in blood vessels elsewhere in the user's body, e.g. the user's brain. The auricle is close to the carotid artery, meaning that ear can be used as a proxy for the vessel condition in the subject's head. Operation of the vascular imaging device of the present invention is also non-invasive, which may improve the comfort and safety of the subject. This may also help to improve the clarity of the obtained image, as the subject may be less likely to move during the imaging process, e.g. as a result of a reflex action.

Generating an image of the blood vessels within the auricle of a human subject is considered to be novel and inventive in its own right. Therefore, when viewed from a third aspect, the invention provides a method of imaging human blood vessels, the method comprising:

- transmitting light to illuminate an auricle of a subject;
- receiving light transmitted through, or reflected from, the auricle and generating image data representative of the received light; and
- generating, from the image data, an image of blood vessels within the auricle of the subject.

Preferably transmitting light to illuminate an auricle of the subject comprises transmitting light from a first side of an auricle of a subject to a second side of the auricle. Receiving light transmitted through the auricle may comprise receiving light at the second side of the auricle. Receiving light reflected from the auricle may comprise receiving light at the first side of the auricle. Preferably the second side of the auricle is opposite the first side of the auricle.

In some embodiments, the method further comprises determining, from the image data, a value representative of a property of a blood vessel of the subject. The method may comprise determining, from the image data, a value representative of a property (e.g. blood oxygenation) of the blood of the subject (e.g. within the blood vessel). In some embodiments, the method comprises comparing the image data and/or the image with sample image data and/or a sample image. The method may comprise analysing the image data and/or the image (e.g. with the sample image data and/or the sample image) to determine an indication of a symptom of a clinical condition. In some embodiments, the method comprises identifying, from the indication of the symptom (e.g. in combination with other metrics or information relating to the subject, such as weight, height or age), said clinical condition in the human subject.

Features of any aspect or embodiment described herein may, wherever appropriate, be applied to any other aspect or embodiment described herein. Where reference is made to different embodiments or sets of embodiments, it should be understood that these are not necessarily distinct but may overlap.

An embodiment of the invention will now be described, by way of example only, with reference to the accompanying drawings, in which.

Figure 1:
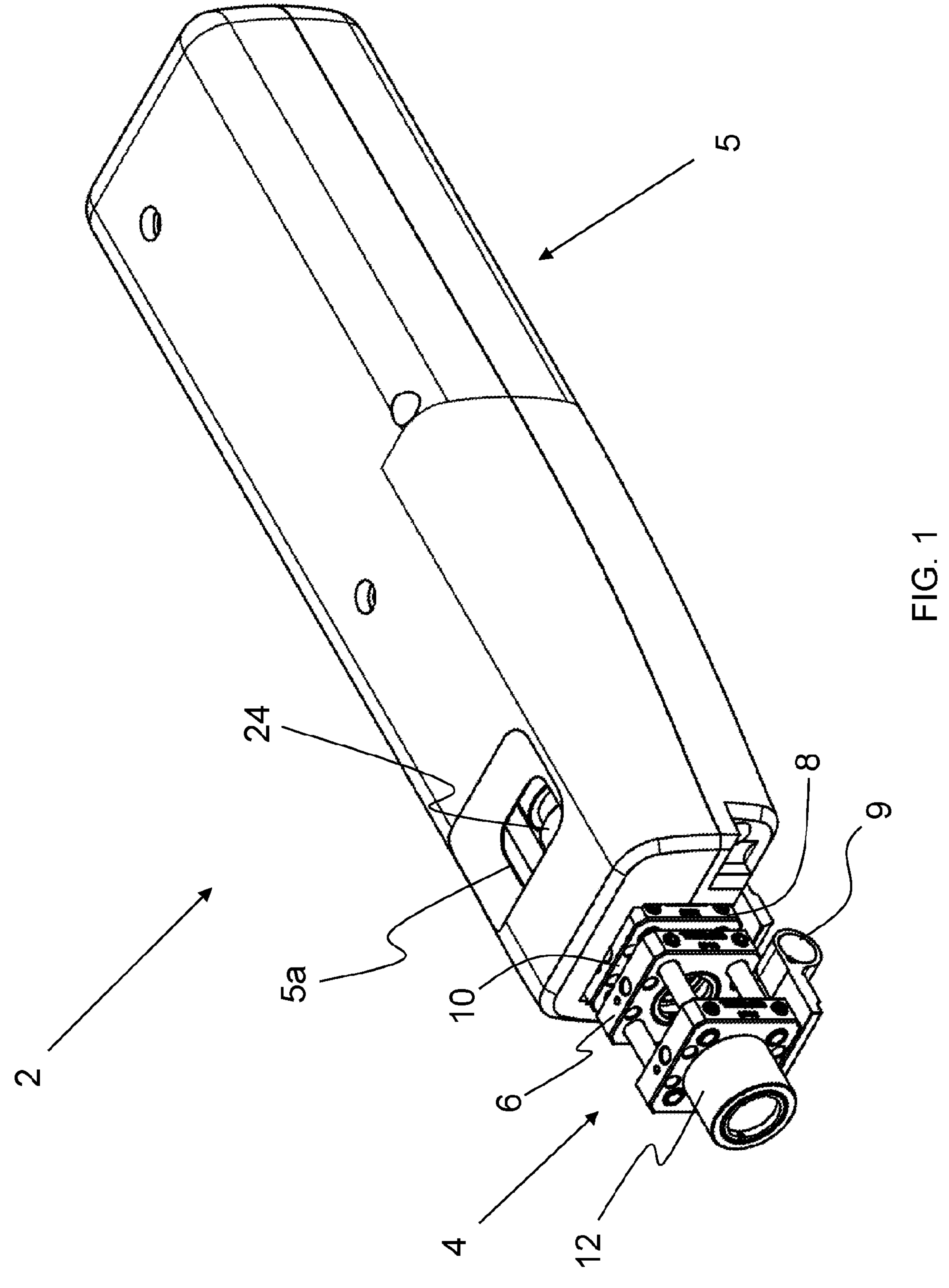
FIG. 1 shows a perspective view of a vascular imaging device in accordance with an embodiment of the present invention.
Figure 3:
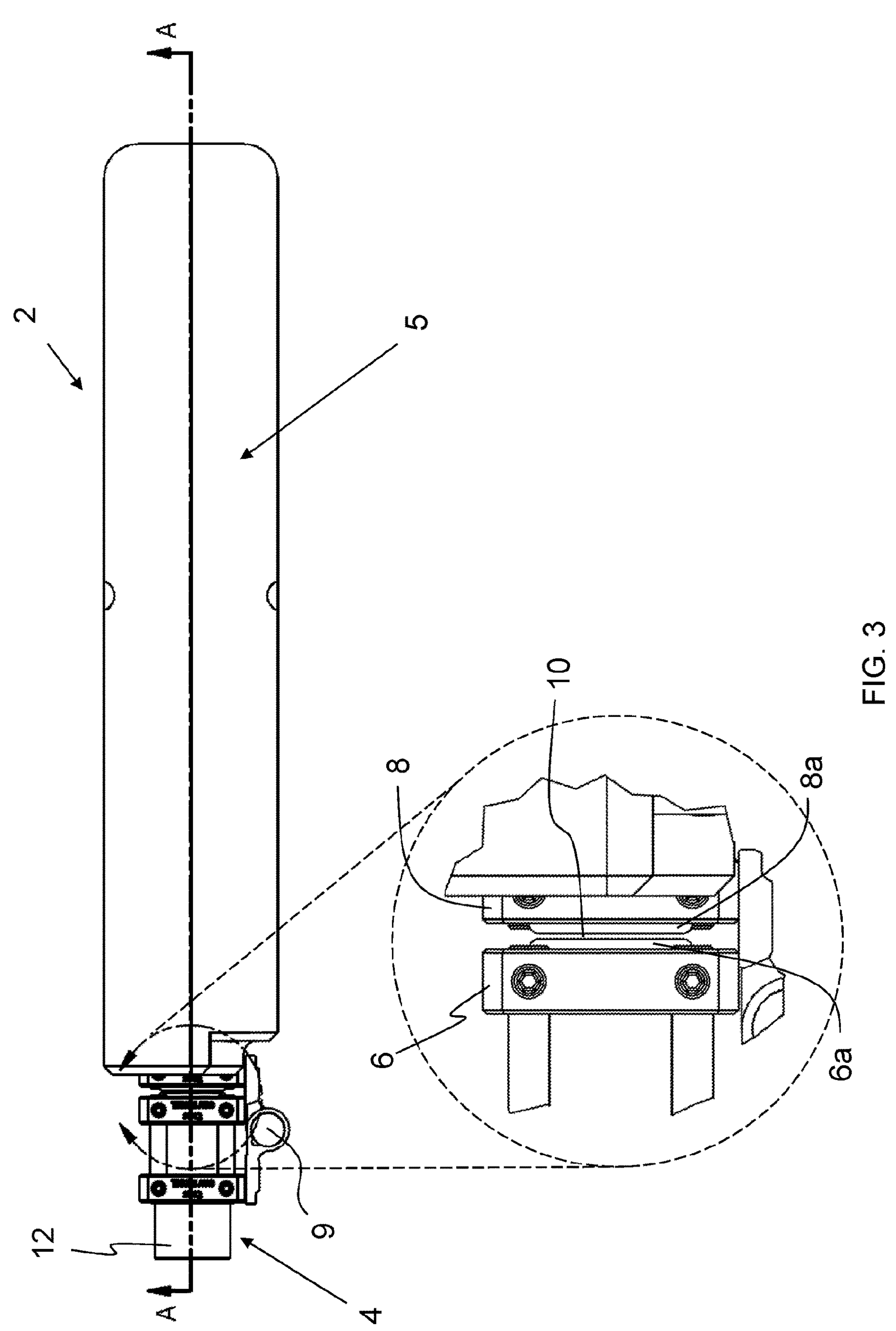
FIG. 3 shows a side view of the vascular imaging device of FIG. 1, including a detailed view of the clamping mechanism.
Figure 4A:
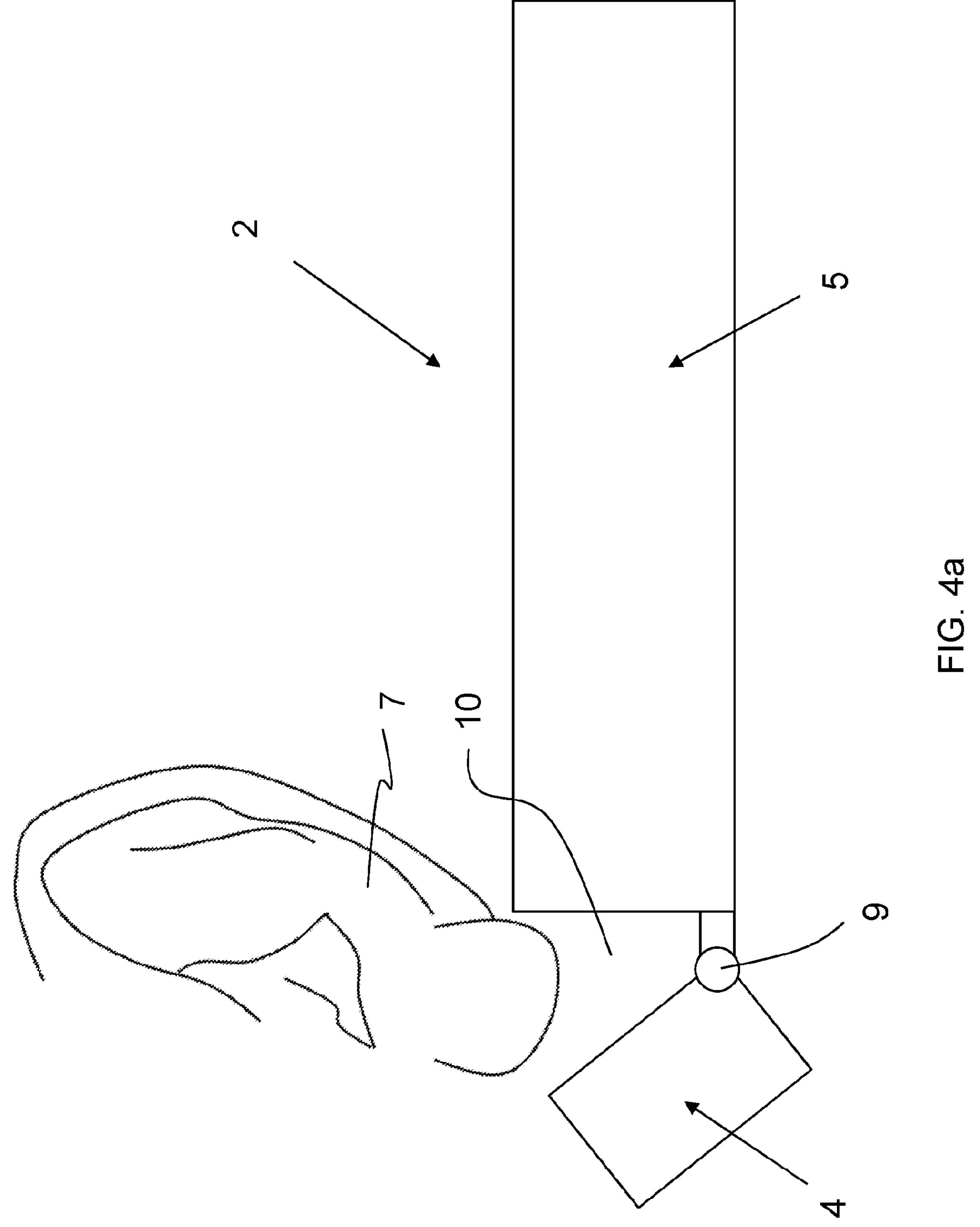
Figure 4B:
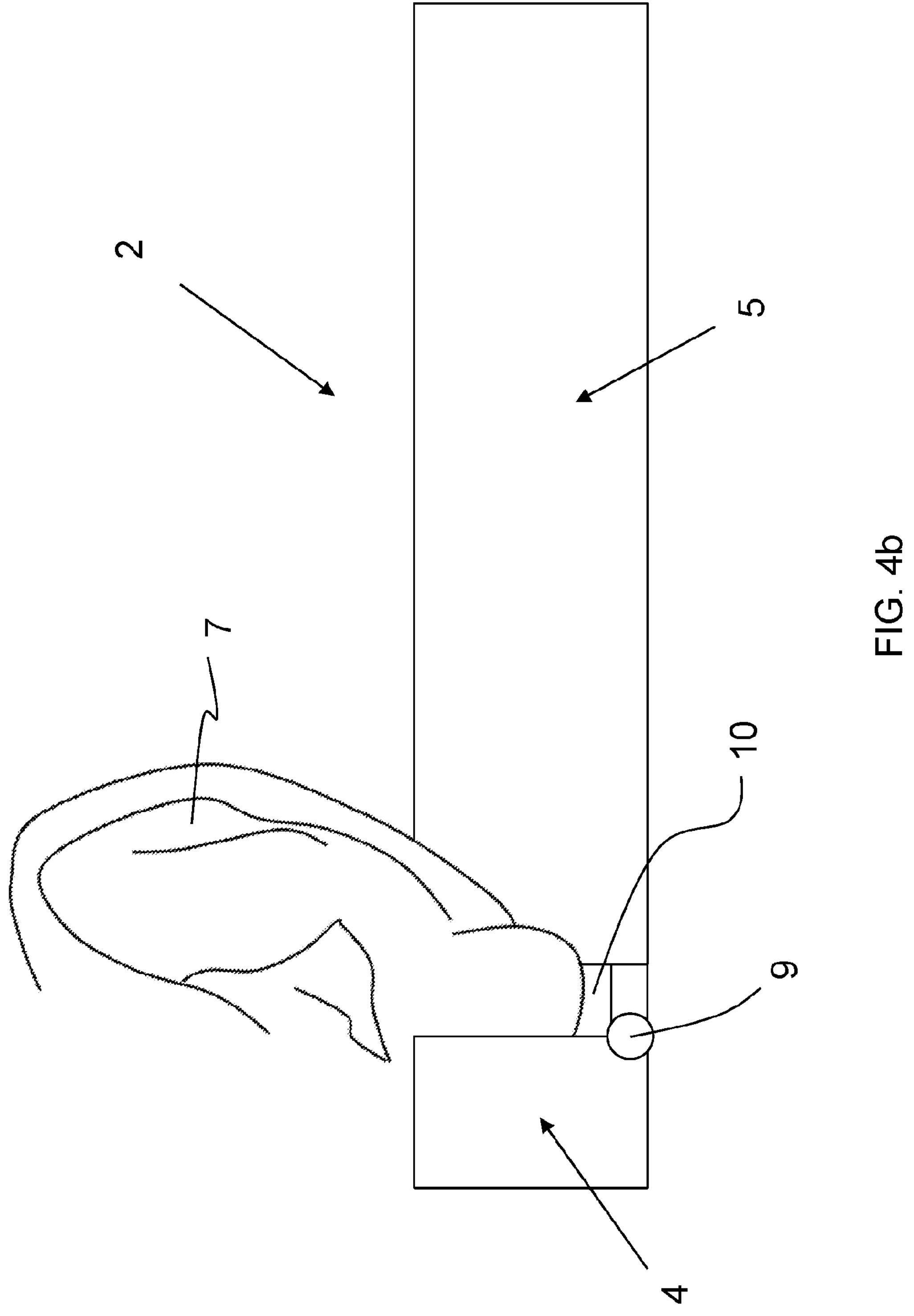
Figure 5:
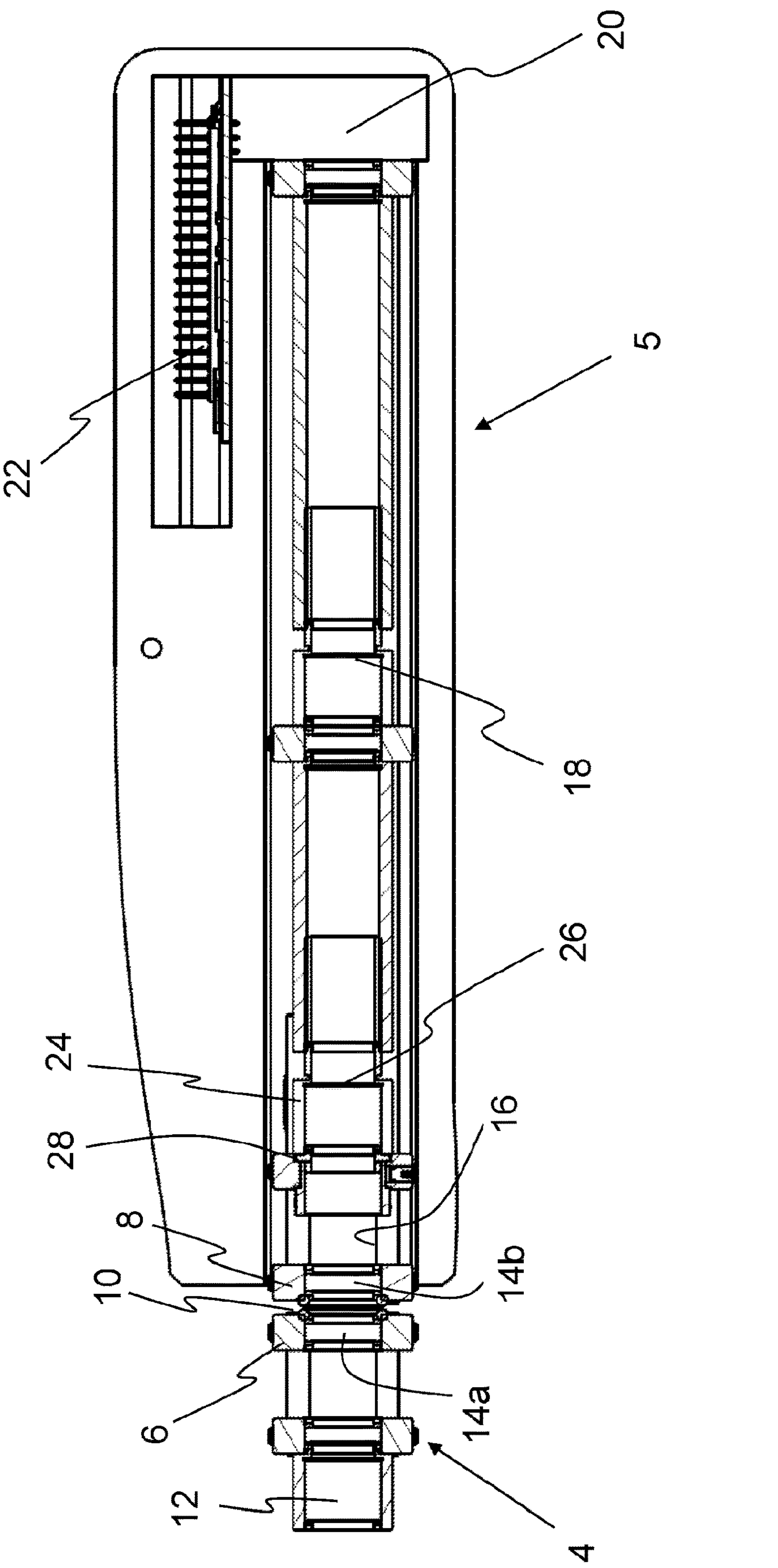
Figure 6:
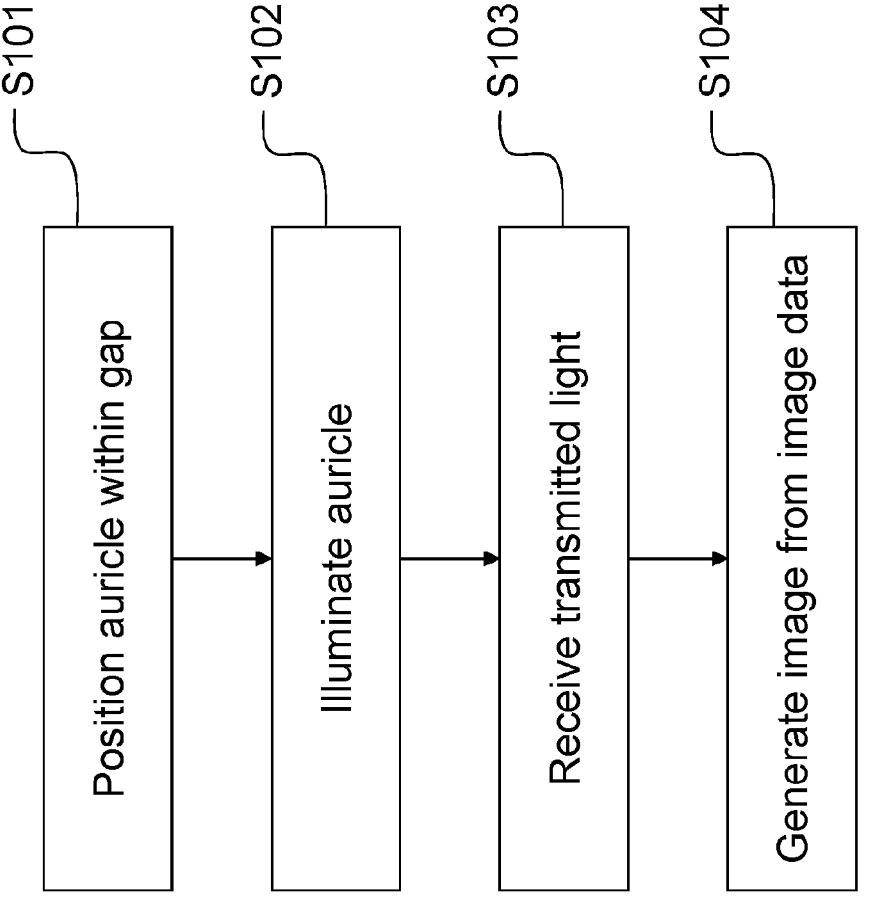
Figure 7:
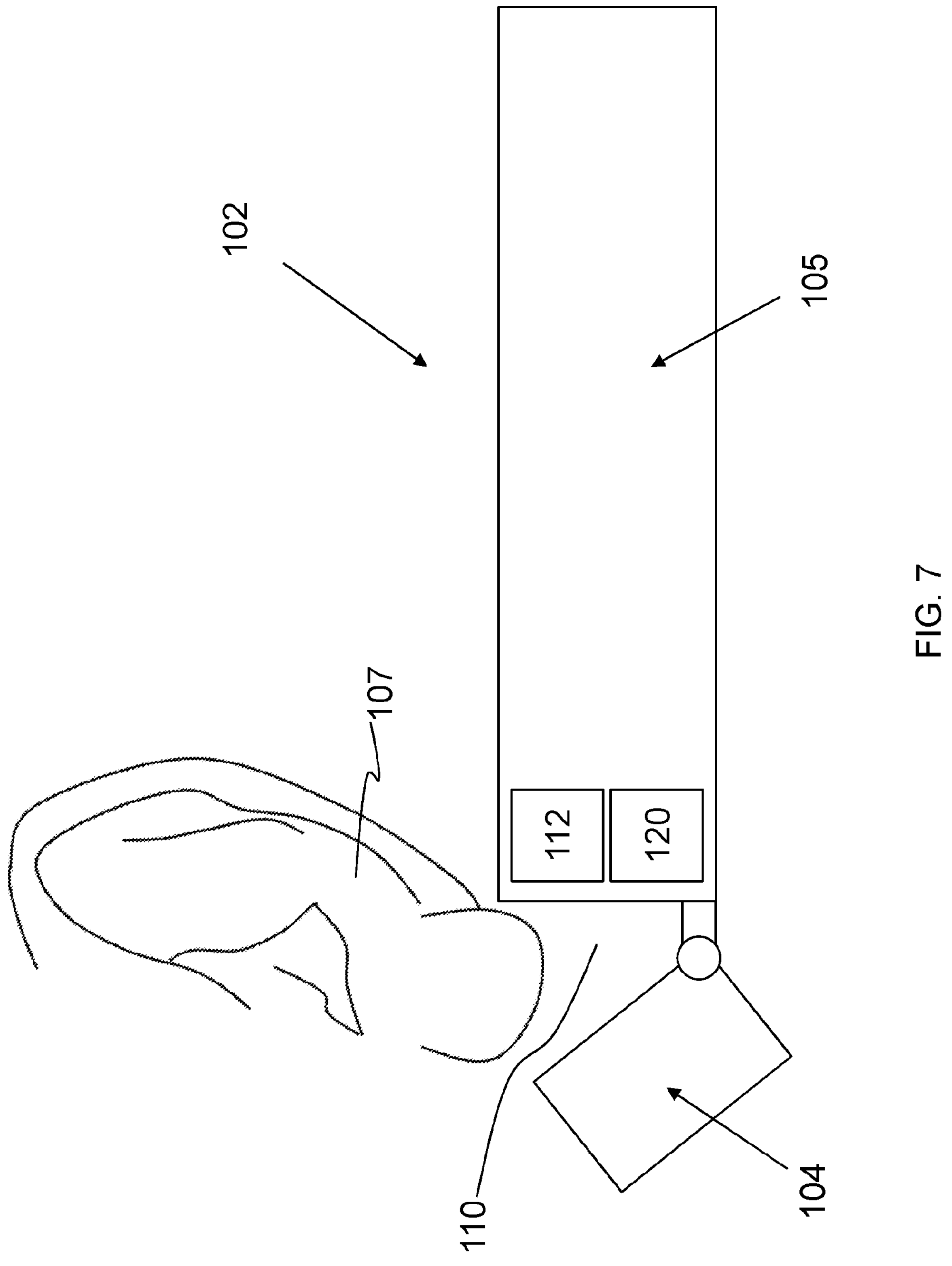
Figure 8:
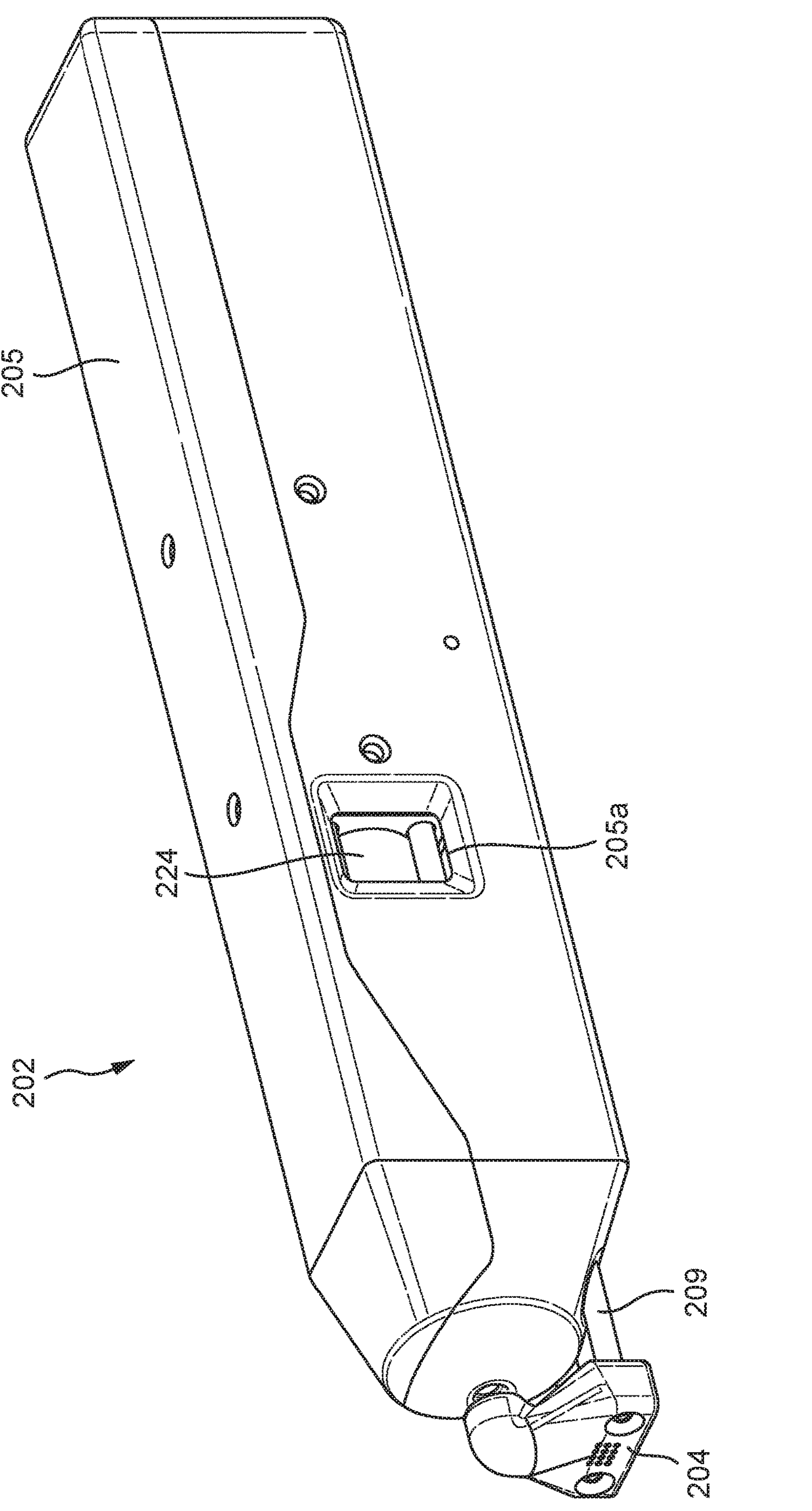
Figure 9:
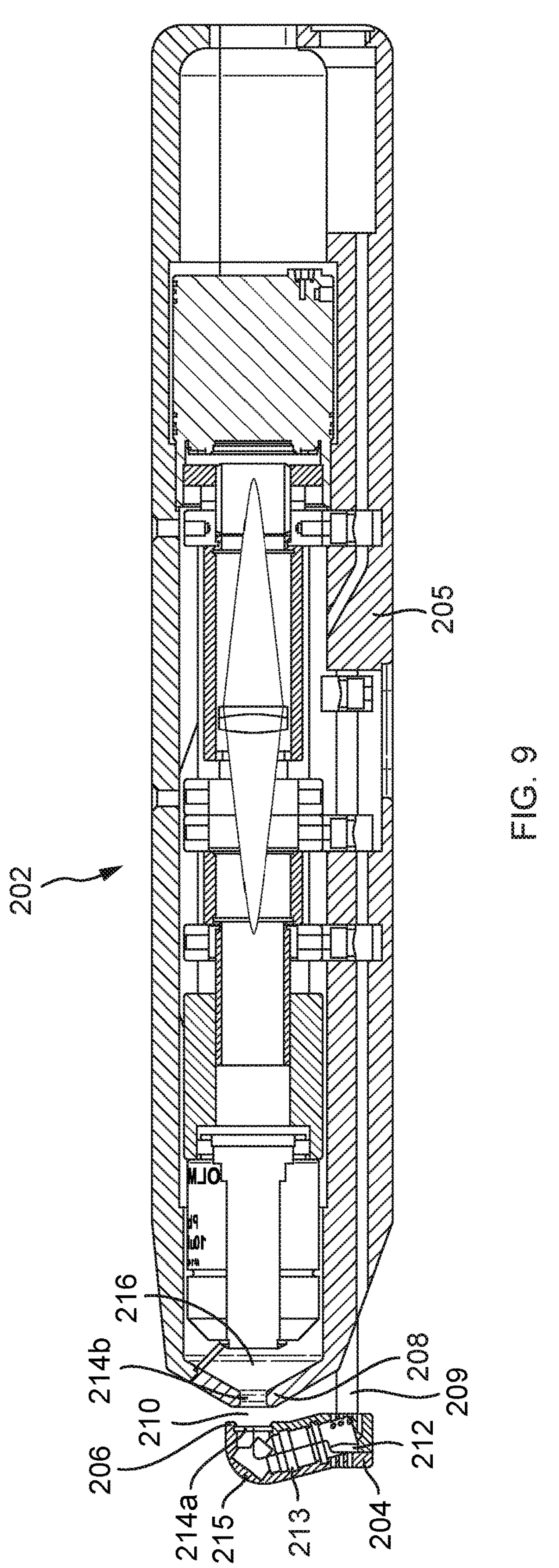

FIGS. 4*a* and 4*b* show schematic views of the device of FIG. 1 in respective unclamped and clamped positions;

FIG. 5 shows a cross-sectional view (section A-A as shown in FIG. 3) of the device of FIG. 1;

FIG. 6 shows a flow diagram illustrating a method in accordance with an embodiment of the present invention;

FIG. 7 shows a schematic view of a vascular imaging device in accordance with another embodiment of the present invention;

FIG. 8 shows a perspective view of a vascular imaging device in accordance with another embodiment of the present invention;

FIG. 9 shows a cross-sectional view of the device of FIG. 8; and

Figure 10A:
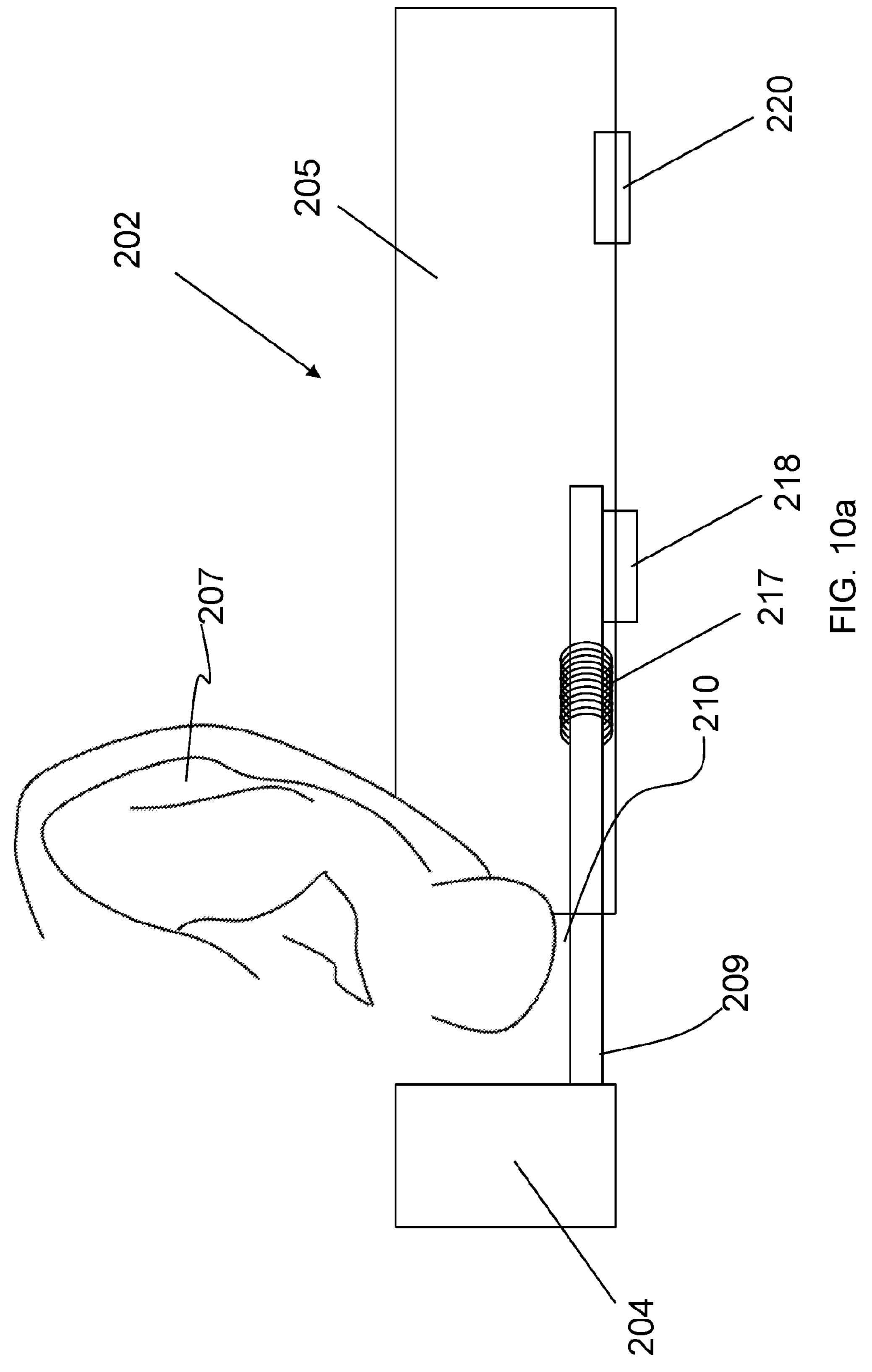
Figure 10B:
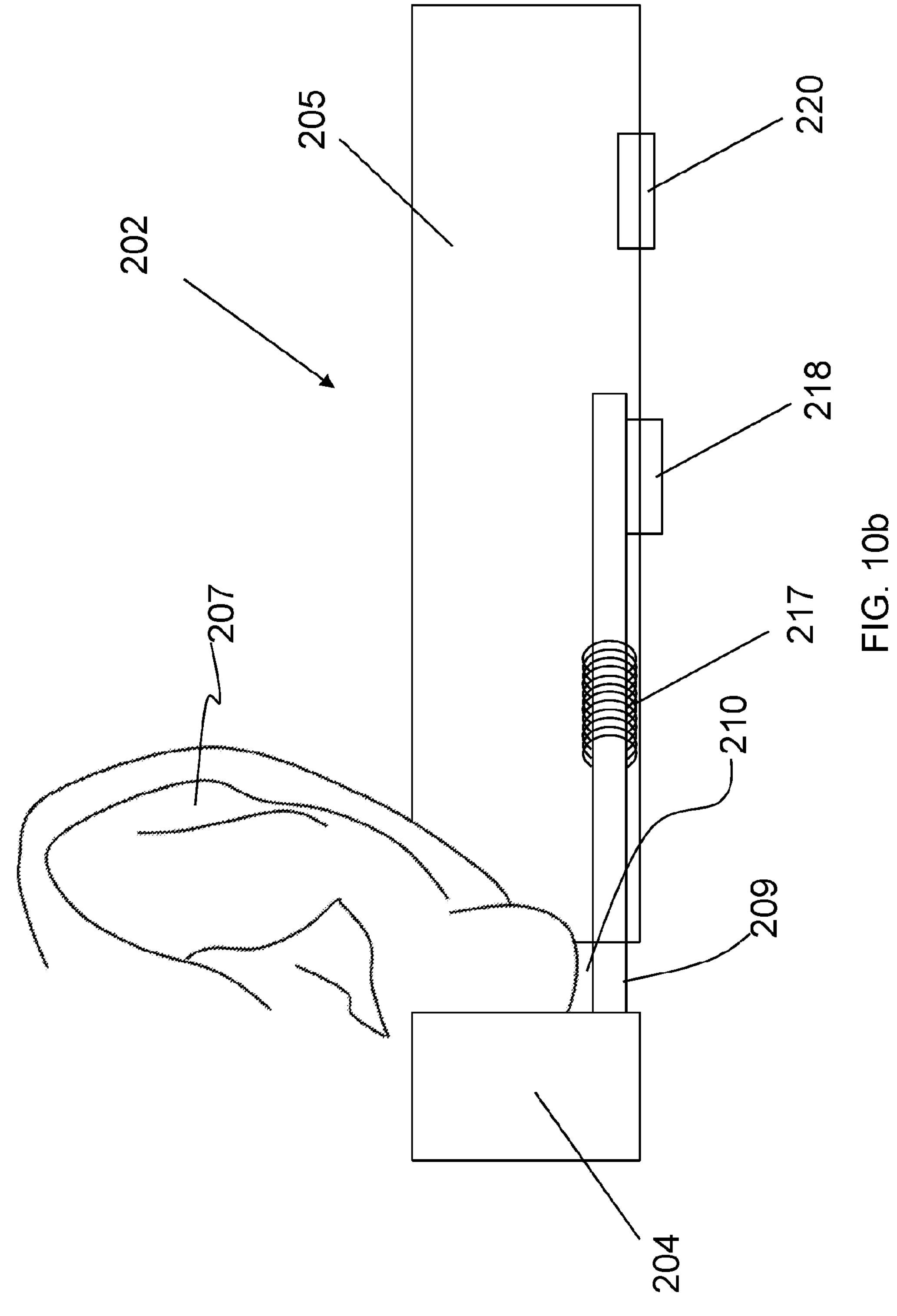

FIGS. 10*a* and 10*b* show schematic views of the device of FIG. 8 in respective unclamped and clamped positions.

The imaging of blood vessels is an important tool for the diagnosis, prevention and monitoring of various conditions and diseases. Conventional vascular imaging techniques can be expensive and time-consuming, which hinders the ability of clinicians to provide care for their patients. The present invention provides a device that is able to collect vascular imaging data reliably and accurately in a timely fashion without incurring significant expense.

FIG. 1 shows a perspective view of a vascular imaging device 2 in accordance with an embodiment of the present invention. The embodiment shown in FIG. 1 is configured for transmission imaging methods, as will be described in more detail below. The device 2 comprises a first casing portion 4 and a second casing portion 5. The first casing portion 4 is hingedly mounted to the proximal end of the second casing portion 5 by a hinge 9. A first clamping member 6 is fixedly mounted to an end of the first casing portion 4 that is proximal to the gap 10 and the optical axis.

The device 2 further comprises a second clamping member 8, mounted to the proximal end of the second casing portion 5.

The first casing portion 4 is hingedly movable between a clamped position, in which the first clamping member 6 is parallel to the second clamping member 8, and an unclamped position, in which the first clamping member 6 is rotated away from the second clamping member 8 about the axis of the hinge 9.

The first and second clamping members 6, 8 are respectively mounted on the first and second casing portions 4, 5 so as to define, in the clamped position, a substantially uniform gap 10 between the opposing surfaces of the first and second clamping members 6, 8. The gap 10 is dimensioned such that the auricle of a human ear can be located within the gap 10.

Figure 2:
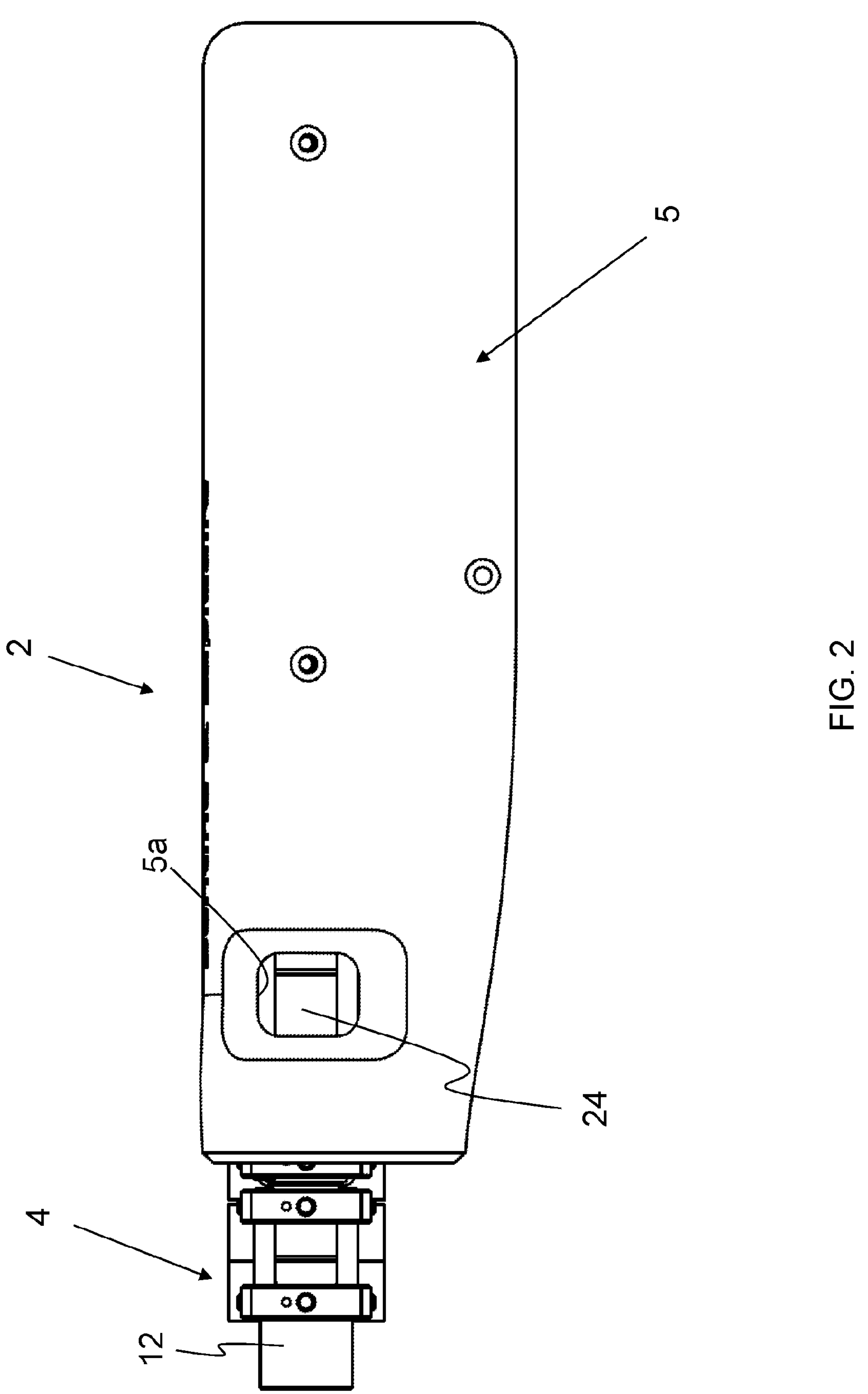
FIG. 2 shows a top view of the vascular imaging device of FIG. 1.

The device 2 further comprises a backlight 12 that is mounted on the first casing portion 4. The second casing portion 5 defines an aperture 5*a* that allows access to a focusing element 24 of the device 2 by an operator. The aperture 5*a* is shown in the top view of the device seen in FIG. 2. The backlight 12 and the focusing element 24 will be described in more detail below.

FIG. 3 shows a side view of the vascular imaging device 2, including a detailed view of the first and second clamping members 6, 8

The first and second clamping members 6, 8 each comprise a respective pad 6*a*, 8*a* mounted on the opposing surfaces of the first and second clamping members 6, 8. The pads 6*a*, 8*a* are manufactured from a soft material, such as rubber or foam, to increase the comfort of the subject while the auricle of the subject is clamped between the first and second clamping members 6, 8.

The hinge 9 comprises a biasing spring (e.g. a torsion spring) (not shown) that biases the first casing portion 4 into the clamped position. This helps to ensure that the auricle of the subject is held tightly between the first and second clamping members 6, 8, which can help to prevent the auricle from moving relative to the device 2 while imaging is being performed. The spring can also help to ensure that the auricle is flattened or (slightly) stretched between the first and second clamping members 6, 8. This can help to improve the quality of the image by reducing the thickness of the auricle and by reducing the intensity of ambient light that is permitted to propagate through the auricle.

In order to position the device 2 for use on a subject, the first casing portion 4 is first pivoted about the hinge 9 to the unclamped position, thus increasing the width of the gap 10 between the first and second casing portions 4, 5. FIG. 4*a* shows a schematic of the device 2 in the unclamped position, before the auricle 7 of a subject has been inserted into the gap 10.

The auricle 7 of the subject is then inserted into the gap 10, before the first casing portion 4 is returned to the clamped position, as shown in FIG. 4*b*. FIGS. 4*a* and 4*b* show the ear lobe of the subject being positioned within the gap 110. However, it will be appreciated that the gap 110 may be arranged to receive any suitable portion of the subject's auricle 7, e.g. the top portion of the auricle 7.

When the first casing portion 4 is returned to the clamped position, the first clamping member 6 is brought into contact with the auricle 7 of the subject. The width of the gap 10 in the clamped position is such that, when the auricle 7 is arranged within the gap 10 and the first casing portion 4 is in the clamped position, the auricle 7 is in contact with both the first clamping member 6 and the second clamping member 8. For example, in the clamped position, the width of the gap 10 may be approximately 8 mm. This helps to ensure that the auricle 7 does not move relative to the device 2 while imaging is performed. This also helps to ensure that ambient light is occluded. Thus, the quality of the image captured can be improved.

FIG. 5 shows a cross-sectional view (section A-A as shown in FIG. 3) of the device 2.

The first clamping member 6 and the second clamping member 8 define respective coaxial circular apertures 14*a*, 14*b*. The second casing portion 5 defines a bore 16 extending from the aperture 14*b* of the second clamping member 8 at the proximal end of the device 2 towards the distal end of the device 2. The bore 16 extends into the second casing portion 5 in a direction perpendicular to the plane of the aperture 14*b*.

The device 2 further comprises a focusing lens 26, a fixed lens 18 and an image sensor 20 mounted within the bore 16 (this order proceeding from the proximal end of the bore 16 to the distal end). The focusing lens 26 and the fixed lens 18 together are arranged to focus the auricle vasculature onto the image sensor 20. The focusing lens 26 is axially linearly movable relative to the fixed lens 18 along the longitudinal axis of the bore 16 by a focusing element 24, which may be manually actuated by the operator of the device 2 or electrically actuated, e.g. using a servo or stepper motor. This movement allows the effective focal length of the optical components to be adjusted, e.g. so that multiple different image "slices" through the depth of the auricle may be captured.

The backlight 12 of the device 2 is a two-colour backlight 12 configured to output red and green light having respective wavelengths of 630 and 523 nanometres. The wavelength of the green light is selected to be close to the wavelength of maximum absorbance for both oxygenated and deoxygenated blood. This increases the contrast between blood vessels and skin tissue, thereby allowing blood vessels to be identified. The wavelength of the red light is selected to allow a distinction to be made between arteries and veins, owing to differences in haemoglobin content.

The red and green wavelengths may be transmitted from the backlight 12 simultaneously or consecutively depending on the type of image sensor 20 used. For a monochromatic image sensor 20, two separate exposures may be required (e.g. illuminating the auricle with green light and obtaining a first image, then illuminating the auricle with red light and obtaining a second image). If a chromatic image sensor 20 is used (e.g. with a Bayer filter), the wavelengths may be transmitted simultaneously and the pixels corresponding to the transmitted wavelengths can be used to generate the image.

The backlight 12 is mounted on the first clamping member 6 and is arranged to direct the red and green light through the aperture 14*a*, the gap 10 (within which the auricle 7 of the subject is positioned), the aperture 14*b* and the bore 16 onto the proximal surface of the focusing lens 26. The light is subsequently directed by the focusing lens 26 and the fixed lens 18 onto the image sensor 20.

The image sensor 20 is configured to produce image data representative of the light received at the image sensor 20 from the backlight 12. It will be appreciated that, when the auricle 7 of the subject is positioned within the gap 10 and is illuminated by the backlight 12, the image data produced by the image sensor 20 can be used to generate an image of the blood vessels within the auricle 7.

The device 2 further comprises polarisation filters 28 that are arranged within the bore 16 of the second casing portion 5 between the aperture 14*b* and the focusing lens 26.

Polarisation imaging methods are sensitive to the birefringence of the blood vessels within the auricle 7 of the subject, which allows further insight into the structure of the subject's blood vessels.

The device 2 further comprises a processor 22, arranged within the second casing portion 5. The processor 22 receives image data from the image sensor 20. The processor 22, image sensor 20 and the backlight 12 are powered by a micro-USB adapter (not shown). The processor 22 is provided with WiFi connectivity so as to allow the processor 22 to communicate wirelessly with a smartphone, tablet or PC.

The processor 22 transmits image data from the sensor 20 to the smartphone in real time for display and/or analysis on a screen of the smartphone. This allows the operator of the device 2 to review the generated image of the subject's auricle 7. This may be for clinical purposes (e.g. to assess changes in the structure of the subject's blood vessels) or to help to ensure proper functioning of the device 2 (e.g. by determining whether the image is in focus).

The processor 22 is configured to calculate from the image data a value representative of the blood vessel density. This may be done by identifying regions of the image that contain blood vessels and calculating a ratio of occupied-area to unoccupied-area of the image. The processor 22 is also configured to analyse the image to determine an estimate of the average blood vessel thickness, for example by tracking the mean vessel thickness of the thickest and thinnest vessels. Automated segmentation methods, which have been developed for retinal imaging, may also be applied to ear vessel images by the processor 22.

Furthermore, the processor 22 is configured to receive command signals from the smartphone for controlling the device 2. For example, the processor 22 may receive a signal instructing the processor 22 to provide power to the backlight 12 and to the image sensor 20 so that imaging of a subject's auricle can be initiated. The processor 22 may also receive a signal instructing the processor 22 to actuate the focusing element 24. Signals such as these may be issued by the smartphone in response to a direct command from a user of the smartphone (e.g. the operator of the device 2), or automatically. For example, the smartphone may issue instructions to the processor 22 to operate the focusing element 24 during the execution of an auto-focus algorithm.

FIG. 6 shows a flow diagram illustrating a method of imaging the blood vessels of a subject, in accordance with an embodiment of the invention.

In the first step S101, the auricle 7 of the subject is positioned within the gap 10 of the device 2. This may involve initially moving the first casing portion 4 to the unclamped position, locating the auricle 7 within the gap 10, and moving the casing portion 4 to the clamped position, such that the first and second clamping members 6, 8 are in contact with respective sides of the auricle 7. Thus, the auricle 7 is held still relative to the device 2 by the first and second clamping members 6, 8.

In the second step S102, power is provided to the backlight 12, which consequently outputs red and green light to illuminate the auricle 7. The light passing through the auricle 7 is focused by the focusing lens 26 and the fixed lens 18 and is detected by the image sensor 20 (S103).

The image sensor 20 is configured to generate image data representative of the light received at the image sensor 20. The processor 22 is configured to process image data output by the image sensor in order to generate an image of the subject's blood vessels (S104). In preferred embodiments, the image is sent wirelessly to an external device (e.g. a smartphone or PC) for display, thereby allowing a clinician to analyse the image.

Once satisfactory image data has been produced, the auricle 7 of the subject is removed from the device 2 by moving the first casing portion 4 to the unclamped position and withdrawing the auricle 7 from the gap 10.

FIG. 7 shows a schematic view of a vascular imaging device 102 in accordance with another embodiment of the present invention. The embodiment shown in FIG. 7 is configured for reflection imaging methods.

The device 102 is essentially the same as the device 2 of FIG. 1, and comprises a first casing portion 104 and a second casing portion 105 (together defining a gap 110), a light source 112 and an image sensor 120. However, in this embodiment, both the light source 112 and the image sensor 120 are mounted on the second casing portion 105.

FIG. 7 shows the first casing portion 104 in its unclamped position. When the auricle 107 is inserted into the gap 110 and the first casing portion 104 is moved to the clamped position, the auricle 107 is held within the gap 110 by the first casing portion 104 and the second casing portion 105. The light source 112 is arranged to direct light into the gap 110 to illuminate the auricle 107. The image sensor 120 is arranged to detect light reflected from the auricle 107 and to generate image data representative of the received light. It will be appreciated that the present invention can improve the quality of images generated using light reflection methods, as the auricle 107 of the subject is held still relative to the image sensor 120 by the first casing portion 104 and the second casing portion 105.

FIG. 8 shows a schematic view of a vascular imaging device 202 in accordance with another embodiment of the present invention. FIG. 9 shows a cross-sectional view of the device of FIG. 8. The embodiment shown in FIGS. 8 and 9 is similar to the device shown in FIGS. 1 to 5, e.g. it is configured for transmission imaging methods.

The device 202 comprises a first casing portion 204 and a second casing portion 205. The first casing portion 204 is slidably mounted to the second casing portion 205 by a rod 209. A first clamping member 206 is fixedly mounted to an end of the first casing portion 204 that is proximal to the gap 210 and the optical axis. The device 202 further comprises a second clamping member 208, mounted to the proximal end of the second casing portion 205.

The first casing portion 204 is slidably movable between a clamped position, in which the first clamping member 206 is closer to the second clamping member 208, and an unclamped position, in which the first clamping member 206 is slid further away from the second clamping member 208.

The first and second clamping members 206, 208 are respectively mounted on the first and second casing portions 204, 205 so as to define, in the clamped position, a substantially uniform gap 210 between the opposing surfaces of the first and second clamping members 206, 208. The gap 210 is dimensioned such that the auricle of a human ear can be located within the gap 210.

The device 202 further comprises a backlight 212 that is mounted on the first casing portion 204. The second casing portion 205 defines an aperture 205*a* that allows access to a focusing element 224 (e.g. a thumbwheel) of the device 202 by an operator. The backlight 212 will be described in more detail below.

The first and second clamping members 206, 208 each comprise a respective pad mounted on the opposing surfaces of the first and second clamping members 206, 208. The pads are manufactured from a soft material, such as rubber or foam, to increase the comfort of the subject while the auricle of the subject is clamped between the first and second clamping members 206, 208.

The pads are shaped and positioned relative to each other so that they mate with each other. Furthermore, in both the clamped and unclamped positions, the opposing surfaces of the first and second clamping members 206, 208 remain parallel to each other. This helps to apply even pressure to the auricle of the subject, while the auricle of the subject is clamped between the first and second clamping members 206, 208, which helps to provide even illumination to the auricle and helps to clamp the auricle flat with respect to (and the auricle perpendicular to the optical axis of) the imaging system.

As shown in FIGS. 8 and 9, the second casing portion 205 has a conical form that tapers towards the second clamping member 208. Similarly, the first casing portion 204 is tapered towards the optical axis. This helps to locate the device around the auricle of a subject and presents a smaller clamping area than the cross-sectional area of the main body of the device, thus allowing it to be used with smaller auricles.

The imaging, polarisation, sensor, processing and/or data capture systems of the device 202 shown in FIGS. 8, 9, 10*a* and 10*b* may be similar to those in the device shown in FIGS. 1 to 5.

The illumination system of the device 202 shown in FIGS. 8, 9, 10*a* and 10*b* differs from the device shown in FIGS. 1 to 5, as will now be described.

In the device 202 shown in FIGS. 8, 9, 10*a* and 10*b*, the backlight 212 (e.g. one or more LEDs configured to output red and green light) is mounted in the first casing portion 204 away from the optical axis. A lens 213 and a mirror 215 are also mounted in the first casing portion 204 to direct the light from the backlight 212 through coaxial circular apertures 214*a*, 214*b* defined in the first clamping member 206 and the second clamping member 208 respectively, and into a bore 216 defined in the second casing portion 205 that extends from the aperture 214*b* of the second clamping member 208 at the proximal end of the device 202 towards the distal end of the device 202. The light is subsequently directed by lenses in the second casing portion 205 onto an image sensor (e.g. in a similar manner as described above with reference to the device shown in FIGS. 1 to 5).

Folding the optical path in this way from the backlight 212 to the aperture 214*a* in the first clamping member 206 helps to keep the first casing portion 204 thin, so that it is more easily able to fit behind the auricle of a subject. This configuration also moves the backlight 212 (and the heat it emits) away from the auricle and head of a subject, which helps to improve the subject's comfort.

FIGS. 10*a* and 10*b* show the device 202 schematically, with the ear lobe of a subject being positioned within the gap 210.

The second casing portion 205 comprises a biasing spring 217 (e.g. a compression spring) (shown in FIGS. 10*a* and 10*b*) that acts on the rod 209 to bias the first casing portion 204 into the clamped position. This helps to ensure that the auricle of the subject is held tightly between the first and second clamping members 206, 208, which can help to prevent the auricle from moving relative to the device 202 while imaging is being performed. The spring 217 can also help to ensure that the auricle is flattened or (slightly) stretched between the first and second clamping members 206, 208. This helps to improve the quality of the image by reducing the thickness of the auricle and by reducing the intensity of ambient light that is permitted to propagate through the auricle.

An actuator 218 (shown in FIGS. 10*a* and 10*b*) is provided to allow a user to move the first casing portion 204 into the unclamped position against the bias of the spring 217, i.e. to increase the gap 210 between the first and second clamping members 206, 208 (as shown in FIG. 10*a*).

In order to position the device 202 for use on a subject, the first casing portion 204 is first slid (through actuation of the actuator 218 against the bias of the spring 217) to the unclamped position, thus increasing the width of the gap 210 between the first and second casing portions 204, 205. FIG. 10*a* shows the device 202 in the unclamped position, as the auricle 207 of a subject is inserted into the gap 210.

The auricle 207 of the subject is inserted into the gap 210, before the first casing portion 204 is returned to the clamped position, through the bias of the spring 217, as shown in FIG. 10*b*. FIGS. 10*a* and 10*b* show the ear lobe of the subject being positioned within the gap 210. However, it will be appreciated that the gap 210 may be arranged to receive any suitable portion of the subject's auricle 207, e.g. the top portion of the auricle 207.

When the first casing portion 204 is returned to the clamped position, the first clamping member 206 is brought into contact with the auricle 207 of the subject, with the spring 217 biasing the clamping members 206, 208 against the auricle 207.

This helps to ensure that the auricle 207 does not move relative to the device 202 while imaging is performed. This also helps to ensure that ambient light is occluded. Thus, the quality of the image captured can be improved.

The second casing portion 205 comprises a button 220 for capturing images of the illuminated auricle. Along with the focusing element 224 and the actuator 218, the button 220 helps to enable the device to be used with a single hand.

Operation of the device 202 shown in FIGS. 8, 9, 10*a* and 10*b* is thus similar to the operation of the device shown in FIGS. 1 to 5.

The invention claimed is:

1. A vascular imaging device comprising:

a casing, comprising a first casing portion and a second casing portion, wherein:

the first casing portion and the second casing portion together define a gap therebetween for receiving an auricle of a subject, and wherein the second casing portion narrows in the direction of the gap; and the first casing portion is slidably movable relative to the second casing portion between an unclamped position, in which the first casing portion is moved away from the second casing portion, and a clamped position, in which the first casing portion is moved towards the second casing portion;

a biasing member arranged to bias the first casing portion into the clamped position; and a rod that extends between the first casing portion and the second casing portion, wherein the rod is slidably mounted to the first casing portion and/or the second casing portion, so to slidably move the first casing portion relative to the second casing portion;

a light source, mounted on the casing; and an image sensor, mounted on the casing;

wherein the light source is arranged to transmit light to illuminate an auricle placed within the gap; and wherein the image sensor is arranged to:

detect light transmitted by the light source; and output image data representative of the light received at the image sensor.

2. The device as claimed in claim 1, wherein the light source is mounted on the first casing portion and the image sensor is mounted on the second casing portion.

3. The device as claimed in claim 1, wherein the device comprises a first clamping member mounted on the first casing portion and a second clamping member mounted on the second casing portion.

4. The device as claimed in claim 1, wherein the first casing portion tapers towards an end of the first casing portion that is proximal to the gap.

5. The device as claimed in claim 1, wherein the light source is spaced from an optical axis of the device.

6. The device as claimed in claim 5, wherein the device comprises one or more lenses, one or more optical fibres and/or one or more mirrors that are arranged to direct light from the light source to the image sensor.

7. The device as claimed in claim 1, wherein the device comprises one or more lenses for focusing an image of the auricle onto the image sensor.

8. The device as claimed in claim 7, wherein one or more of the lenses are movable relative to the light source, the gap and/or the image sensor.

9. The device as claimed in claim 1, wherein the device comprises a polarisation filter mounted on the device between the image sensor and the gap.

10. The device as claimed in claim 1, wherein the device comprises a processor configured to process image data received from the image sensor.

11. The device as claimed in claim 10, wherein the processor is configured to analyse the image data to determine a value representative of a property of a blood vessel of the subject.

12. The device as claimed in claim 1, wherein the device comprises a transmitter and/or a receiver configured communicate with an external device or server.

13. The device as claimed in claim 1, wherein the device comprises an integral power supply.

14. The device as claimed in claim 1, wherein the gap is defined between opposing surfaces of the first casing portion and the second casing portion, and wherein one or both opposing surfaces comprises a soft padding material.

15. A method of operating a vascular imaging device, the device comprising:

a casing, comprising a first casing portion and a second casing portion, wherein:

the first casing portion and the second casing portion together define a gap therebetween for receiving an auricle of a subject, and wherein the second casing portion narrows in the direction of the gap; and the first casing portion is slidably movable relative to the second casing portion between an unclamped position, in which the first casing portion is moved away from the second casing portion, and a clamped position, in which the first casing portion is moved towards the second casing portion;

a biasing member arranged to bias the first casing portion into the clamped position; and a rod that extends between the first casing portion and the second casing portion, wherein the rod is slidably mounted to the first casing portion and/or the second casing portion, so to slidably move the first casing portion relative to the second casing portion;

a light source, mounted on the casing; and an image sensor, mounted on the casing;

wherein the light source is arranged to transmit light to illuminate an auricle placed within the gap and the image sensor is arranged to detect light transmitted by the light source and to output image data representative of the light received at the image sensor;

the method comprising:

positioning an auricle of a subject within the gap;

receiving, at the image sensor, light transmitted from the light source through, or reflected from, the auricle;

generating, from image data provided by the image sensor, an image of blood vessels within the auricle.

* * * * *